United States Patent [19]

Englert et al.

[11] Patent Number: 4,942,176

[45] Date of Patent: Jul. 17, 1990

[54] N-SUBSTITUTED AMINOALKANOIC ACIDS, A PROCESS FOR THEIR PREPARATION, THEIR USE AND PHARMACEUTICAL PRODUCTS BASED ON THESE COMPOUNDS

[75] Inventors: Heinrich C. Englert, Hofheim am Taunus; Max Hropot, Flörsheim am Main; Hans-Jochen Lang, Hofheim am Taunus; Rainer Greger, Heitersheim, all of Fed. Rep. of Germany

[73] Assignee: Hoechst Aktiengellschaft, Frankfurt am Main, Fed. Rep. of Germany

[21] Appl. No.: 348,115

[22] Filed: May 4, 1989

Related U.S. Application Data

[63] Continuation of Ser. No. 25,582, Mar. 13, 1987, abandoned.

[30] Foreign Application Priority Data

Mar. 15, 1986 [DE] Fed. Rep. of Germany ........ 3608725

[51] Int. Cl.$^5$ ............................................. C07C 101/78
[52] U.S. Cl. ..................................... 514/539; 514/567
[58] Field of Search .................... 560/43, 36; 514/541, 514/539, 567; 562/441

[56] References Cited

U.S. PATENT DOCUMENTS 3,632,636 1/1972 Wei et al. ............................ 562/441

FOREIGN PATENT DOCUMENTS 2016448 9/1979 United Kingdom .
1585965 3/1981 United Kingdom .

OTHER PUBLICATIONS

Allan et al., Medical Research Reviews, vol. 3, No. 2, 91–118 (1983).
Wangemann et al., "Cl$^-$–Channel Blockers in the Thick Ascending Limb of the Loop of Henle. Structure Activity Relationship", 1986, pp. 128–141.

Primary Examiner—Bruce Gray
Attorney, Agent, or Firm—Finnegan, Henderson, Farabow, Garrett, and Dunner

[57] ABSTRACT

A description is given of a process for the preparation of a compound of the formula I

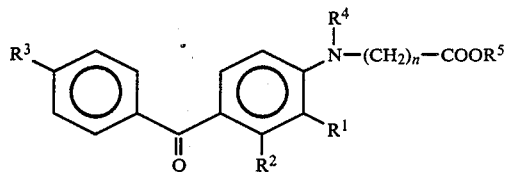

in which $R^1$, $R^2$ and $R^3$ (identical or different) represent H, alkyl having 1–2 carbon atoms and F, Cl, Br or I;
$R^4$ represents H, alkyl having 1–4 carbon atoms, n represents the numbers 2–5, and
$R^5$ represents a radical which can be eliminated under physiological conditions or represents hydrogen, and its physiologically tolerated salts.

They are effective remedies for diarrhea.

1 Claim, No Drawings

N-SUBSTITUTED AMINOALKANOIC ACIDS, A PROCESS FOR THEIR PREPARATION, THEIR USE AND PHARMACEUTICAL PRODUCTS BASED ON THESE COMPOUNDS

This application is a continuation of application Ser. No. 025,582, filed Mar. 13, 1987, now abandoned.

The invention relates to N-substituted amionalkanoic acids of the formula I

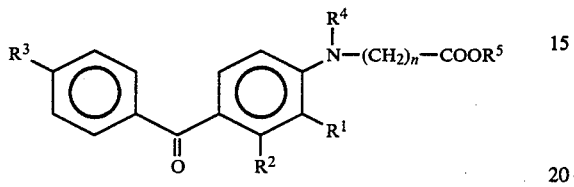

in which
R$^1$, R$^2$ and R$^3$ are identical or different and represent H, alkyl having 1-2 carbon atoms and F, Cl, Br or I, R$^4$ represents H or alkyl having 1-4 carbon atoms, n represents the numbers 2-5, and R$^5$ represents hydrogen or a radical which can be eliminated under physiological conditions, and to their physiologically tolerated salts.

Compounds of the formula I are new. Compounds in which n represents 3 may formally be regarded as N-substituted γ-aminobutyric acids (GABA). Numerous derivatives of GABA have been described in the literature, including those which have the n-butyl or 2-phenylethyl radical on the amine nitrogen (Medicinal Research Reviews, Vol. 3, No. 2, 91–118 (1983)) and thus resemble or are similar to the compound I according to the invention. Compounds of this type stand in connection with structure-effect relations of GABA as neurotransmitter, where attention has been drawn to some of them as weak GABA antagonists. In terms of pharmacology, this should be regarded as indicating a convulsive effect of the compound.

Thus it was entirely surprising to find that the compounds I according to the invention, despite their similarity with the abovementioned GABA antagonists, do not have an undesired convulsive effect but, on the contrary, have proven suitable for the treatment of diarrhea, in particular those types of diarrhea caused by bacteriotoxins such as, for example, cholera toxin. In addition, further therapeutically utilizable effects such as, for example, saluresis, diuresis, an antipyretic effect and an inhibitory effect on excessive sweat production have been observed.

Preferred compounds of the formula I are those in which at least one of the substituents has the following meaning: R$^1$, R$^2$ and R$^3$ (identical or different) hydrogen, F, Cl, Br or I, R$^4$ H or methyl, R$^5$ (C$_1$–C$_8$)alkyl, straightchain or branched, and n equal to 3.

The invention also relates to a process for the preparation of N-arylaminoalkanoic acids, which comprises
(a) benzoylation of compounds of the formula II

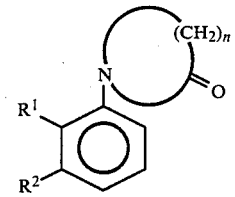

to give compounds III

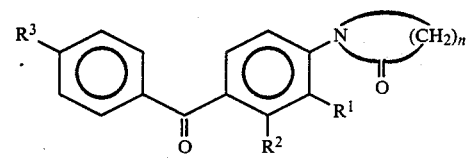

and hydrolytic ring-opening of the latter to give compounds I,
(b) reaction of compounds of the formula IV

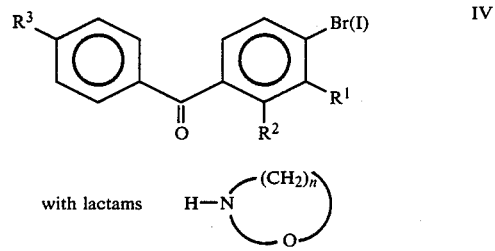

to give compounds III, and hydrolytic ring-opening of the latter to give the compounds I
(c) reaction of amines V

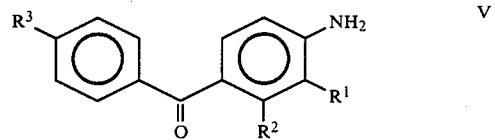

with acrylic acid to give the compounds I
(d) alkylation of compounds of the formula Ia

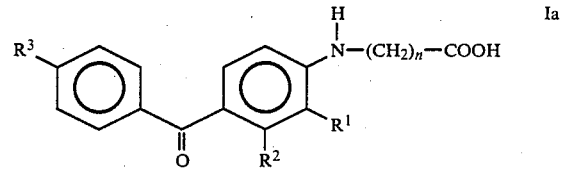

to give compounds Ib

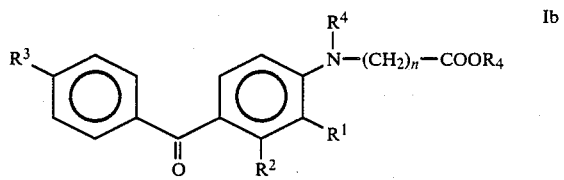

but where R⁴ in this case does not denote hydrogen, and hydrolysis of the latter to give compounds I.

In process (a) the process is advantageously such that compounds of the formula II are reacted, under Friedel-Crafts conditions, with carbonyl chorides VIa, for example in dichloromethane as solvent and with AlCl₃ as catalyst. However, an additional advantageous variant is one which comprises reaction of carboxylic acids VIb

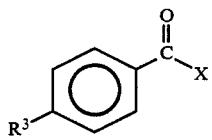

X = Halogen: VIa
X = OH: VIb directly with the compounds II in the presence of polyphosphoric acid. The ring-opening of II is most advantageously carried out by dissolving II in a suitable organic solvent such as, for example, methanol or ethanol, and then adding sufficient aqueous alkali metal hydroxide solution until II just starts to separate out. The mixture is then heated until ring-opening is complete, advantageously at the reflux temperature of the solvent used.

Compounds III can also be prepared by reacting 4-bromo-or 4-iodobenzophenone derivative IV in the manner of the Ullmann-Goldberg reaction with lactams

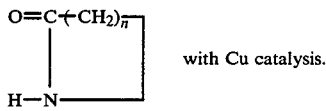

with Cu catalysis.

with Cu catalysis.

Inert solvents such as dimethylformamide are used or, advantageously, a solvent is entirely dispensed with, or excess lactam is used as solvent, which has proven to be very particularly advantageous in practice. The addition of a base, for example of finely powdered potassium acetate or potassium carbonate, is also advantageous for good yields. Elevated temperatures are generally necessary for the reaction, which is advantageously carried out in the range 140°-190° C.

In process variant (c) it is best to react the amine V with the acrylic acid in the presence of weak alkanoic acids such as acetic acid or propionic acid. The reactions generally require elevated reaction temperatures, for example the reflux temperature of the alkanoic acid which is added.

In process variant (d) compounds I in which R⁴ represents H are reacted with 2 equivalents of an alkylating agent R⁴-Y where Y represents a leaving group such as Cl, Br, I, tosylate, mesylate or methylsulfate. This reaction is carried out by standard methods and, in general, initially the carboxyl group is converted into the ester, and only after a prolonged reaction time is the desired N-alkylation obtained too. This reaction is particularly dependent on very weak bases being used as catalyst. Thus, NaHCO₃ in dimethylformamide results in the desired products, whereas, for example, K₂CO₃ in DMF would result in the compounds III which are not desired in this case. The compounds Ib are subjected to alkaline hydrolysis by standard methods, advantageously using aqueous lithium hydroxide solution.

The compounds of the formula I, according to the invention, and their pharmaceutically tolerated salts - particularly suitable in this context are the alkali metal and alkaline earth metal salts such as, for example, Na⁺, K⁺, NH₄⁺ salts, but salts of organic bases such as, for example, the ethanolamine salt are also of importance - are agents for the treatment of diarrhea. They are administered enterally, for example orally, in doses of at least 0.01 mg/kg, preferably 0.05 mg/kg and, in particular, 0.5 mg/kg to a maximum of 200 mg/kg, preferably 50 mg/kg and, in particular, 20 mg/kg body weight based on an adult weighing 75 kg, in capsules, coated tablets, tablets or solutions, alone or in combination with electrolyte solutions which counteract the dehydration associated with diarrhea. They are suitable for the treatment of all diseases in which there is a pathological increase in the loss of water and electrolytes via the intestines, as occurs in the wide variety of types of diarrhea, especially in toxic diarrhea resulting from infectious diseases such as, for example, cholera, or hereditary types of diarrhea, such as congenital chloride diarrhea.

EXAMPLE 1

4-(4-Benzoylanilino)butyric acid 2.61 g (0.01 mole) of 4-bromobenzophenone and 1.13 ml of butyrolactam (0.015 mole) are fused together at 180° C., and 1.4 g of K₂CO₃ and 0.63 g of Cu powder are added. The mixture is stirred at this temperature for 2 h, allowed to cool to 140° C. and then dissolved in ethyl acetate. Chromatography on silica gel eluting with toluene/ethyl acetate provides N-(4-benzoylphenyl)-2-pyrrolidinone of melting point 162°-164° C., which is immediately dissolved in 10 ml of methanol and 10 ml of 5 N NaOH and boiled under reflux for about 2 h. After the methanol has been removed by distillation, the mixture is acidified to pH 5, and the product is filtered off with suction. Melting point: 156°-158° C.

EXAMPLE 2

5-(4-Benzoylanilino)valeric acid

In analogy to Example 1 with valerolactam in place of butyrolactam.

Melting point: 123°-124 C.

EXAMPLE 3

3-(4-Benzoylanilino)propionic acid 1.97 g of 4-aminobenzophenone (0.01 mole) and 1.44 g of acrylic acid (0.02 mole) are dissolved in 10 ml of glacial acetic acid and boiled under reflux for 2 days. The solution is evaporated to dryness in vacuo, and the residue is redissolved in 2 N sodium hydroxide solution, and the solution is extracted several times with diethyl ether. The aqueous solution is adjusted to pH 4-5 with 2 N HCl, and the precipitate is filtered off with suction and washed with water.

Melting point: 139°-141° C.

EXAMPLE 4

4-[4-(4-Methoxybenzoyl)anilino]butyric acid 1.61 g (0.01 mole) of n-phenyl-2-pyrrolidinone and 1.49 g (0.011 mole) of 4-methylbenzoic acid are stirred in 20 ml of polyphosphoric acid at 170° C. for 1 h. The mixture is poured onto ice-water, and the precipitate is filtered off with suction and dissolved in ethyl acetate.

The organic phase is extracted 3 times with saturated NaHCO$_3$ solution, dried with MgSO$_4$, filtered through silica gel (elution with ethyl acetate) and evaporated to dryness in vacuo. The residue is recrystallized from toluene and then hydrolyzed as in Example 1 to give the title compound.

Melting point 185°–186° C.

EXAMPLE 5

4-[4-(4-Chlorobenzoyl)anilino]butyric acid

In analogy to Example 4 the title compound is obtained from 4-chlorobenzoic acid and N-phenyl-2-pyrrolidinone and has the melting point 172°–173° C.

EXAMPLE 6

4-(4-Benzoyl-3-chloroanilino)butyric acid

In analogy to Example 4 the title compound is obtained from benzoic acid and N-(3-chlorophenyl)-2-pyrrolidinone and has the melting point 136°–137° C.

EXAMPLE 7

4-(4-Benzoyl-2-chloroanilino)butyric acid

In analogy to Example 4 the title compound is obtained from benzoic acid and N-(2-chlorophenyl)-2-pyrrolidinone and has the melting point 160°–161° C.

EXAMPLE 8

4-(N-Methyl-4-benzoylanilino)butyric acid 1.41 g (0.05 mole) of 4-(4-benzoylanilino)butyric acid are dissolved in 15 ml of DMF, and 0.84 g of NaHCO$_3$ (0.01 mole) and 1.42 g (0.01 mole) of methyl iodide are added, and the mixture is stirred at 80° C. for about 3 h. It is then poured onto ice-water, the mixture is extracted with ethyl acetate, the organic phase is dried with MgSO$_4$, and the solvent is evaporated off in vacuo. The residue is chromatographed on silica gel using n-hexane/ethyl acetate as eluent. The oily product is immediately hydrolyzed with 2 N LiOH. The title compound is obtained and has the melting point 111°–113° C.

We claim:

1. A method for treating diarrhea or the loss of water and electrolytes which comprises administering to one in need of treatment an effective amount of a compound according to the following formula I:

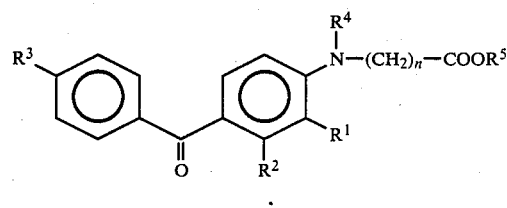

in which

R$^1$, R$^2$ and R$^3$ are identical or different and are H, alkyl having 1–2 carbon atoms, F, Cl, Br or I, R$^4$ is H or alkyl having 1–4 carbon atoms, n is a number from 2 to 5, and R$^5$ is hydrogen or a radical which can be eliminated under physiological conditions, or a pharmaceutically acceptable salt thereof.

* * * * *